(12) United States Patent
Lorusso et al.

(10) Patent No.: US 6,670,612 B1
(45) Date of Patent: Dec. 30, 2003

(54) UNDERCUT MEASUREMENT USING SEM

(75) Inventors: Gian Francesco Lorusso, Fremont, CA (US); Luca Grella, Gilroy, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 0 days.

(21) Appl. No.: 10/186,797

(22) Filed: Jul. 1, 2002

(51) Int. Cl.[7] ............................................. G01N 23/225
(52) U.S. Cl. ..................... 250/310; 250/307; 250/311
(58) Field of Search ............................... 250/307, 310, 250/311, 492.2, 396 R

(56) References Cited

U.S. PATENT DOCUMENTS

| | | | | |
|---|---|---|---|---|
| 4,426,577 A | * | 1/1984 | Koike et al. | 250/310 |
| 5,029,250 A | * | 7/1991 | Komatsu et al. | 250/310 |
| 5,578,821 A | * | 11/1996 | Meisberger et al. | 250/310 |
| 5,739,909 A | * | 4/1998 | Blayo et al. | 356/369 |
| 5,869,833 A | * | 2/1999 | Richardson et al. | 250/310 |
| 6,031,614 A | * | 2/2000 | Michaelis et al. | 356/369 |
| 6,054,710 A | * | 4/2000 | Bruggeman | 250/307 |
| 6,066,849 A | * | 5/2000 | Masnaghetti et al. | 250/310 |
| 6,411,377 B1 | * | 6/2002 | Noguchi et al. | 356/237.4 |
| 6,472,662 B1 | * | 10/2002 | Archie | 250/307 |
| 2002/0151092 A1 | * | 10/2002 | Li et al. | 438/16 |

OTHER PUBLICATIONS

Focused Ion Beam Technology, IBM Microelectronics; Webpage [on–line], [retrieved on Oct. 17, 2002]. Retrieved from the internet: URL:http://www.–3ibm.com/chips/services/asg/capabilites/asweb13.html.

* cited by examiner

*Primary Examiner*—John R. Lee
*Assistant Examiner*—James P. Hughes
(74) *Attorney, Agent, or Firm*—Okamoto & Benedicto LLP

(57) ABSTRACT

The disclosure relates to measuring an undercut of a feature on a specimen using a scanning electron microscope (SEM). In accordance with one embodiment, a method for measuring the undercut includes illuminating the feature with a primary electron beam at an incident angle, changing the incident angle of the primary electron beam over a set of angles, measuring an intensity of scattered electrons from the feature for each incident angle in the set of angles, and determining a discontinuity in the intensities as a function of the incident angle.

20 Claims, 13 Drawing Sheets

UNDERCUT MEASUREMENT USING SEM

BACKGROUND OF THE INVENTION

1. Field of the Invention

The present invention relates generally to specimen inspection.

More particularly, the present invention relates to e-beam inspection systems.

2. Description of the Background Art

Semiconductor manufacturing processes include deposition and etching of various material layers on a semiconductor wafer. During the processing, various microscopic features (trenches, islands, and so on) are created on the wafer. Often times, the cross-sectional profile of a microscopic feature may be of interest to the manufacturer. In particular, the angle of undercut of a sidewall of the feature may be of interest.

Scanning electron microscopy (SEM) may be used to inspect a wafer, and the rock angle of the incident beam may be varied in an attempt to view an undercut. Unfortunately, SEM images tend to have significant resolution degradation when taken at large rock angles. This blurring of the images makes impractical the determination of large undercut angles by viewing SEM images at large rock angles.

Another conventional technique for determining undercut angles is by way of focus ion beam (FIB) sections. FIB systems impinge a focused beam on ions (for example, gallium ions) onto a specimen. The focused ion beam may act to precision mill the specimen at high beam currents or to image the specimen at low beam currents (in which case less material is sputtered). Hence, an FIB system may be used in preparing a cross-section specimen for transmission electron microscope (TEM) imaging. Recent FIB systems may be utilized for in-situ cross-section preparation and high-resolution imaging. However, FIB techniques are disadvantageously destructive due to the sputtering or milling of material from the sample.

FIG. 1A is a conventional image of a cross section of a feature 170 that is slightly undercut on both left and right sides. The image of the cross section was obtained by the conventional focused ion beam (FIB) technique. As mentioned above, the FIB technique is disadvantageous in that it requires destruction of the specimen. This is because the FIB technique thins the sample by ion milling.

FIG. 1B shows a conventional analysis of the cross-sectional FIB image of the feature 170 to determine the undercut angles. The analysis gives an outline of the feature 170. Using the outline of the feature 170, the undercut angle may be determined by comparing the actual left 172-L and right 172-R sidewalls to vertical reference lines 174-L and 174-R, respectively. (The slight asymmetry seen in the reference lines is thought to be due to the milling of the sample.) Analysis of this FIB image indicates a left undercut of about five (5) degrees and a right undercut of about two (2) degrees.

SUMMARY

Embodiments of the invention relates to methods for measuring an undercut of a feature on a specimen using a scanning electron microscope (SEM). One method includes illuminating the feature with a primary electron beam at an incident angle, changing the incident angle of the primary electron beam over a set of angles, measuring an intensity of scattered electrons from the feature for each incident angle in the set of angles, and determining a discontinuity in the intensities as a function of the incident angle. Another method includes illuminating the feature with primary electrons at an incident angle, measuring an intensity of scattered electrons from the feature by a plurality of detectors at a set of scattering angles, and determining a discontinuity in the intensities as a function of the scattering angle.

Another embodiment of the invention relates to a scanning electron microscope (SEM) for measuring an undercut of a feature on a specimen. The SEM includes an electron illumination system for illuminating the feature with a primary electron beam at an incident angle, a mechanism for changing the incident angle of the primary electron beam over a set of angles, a detector for measuring an intensity of scattered electrons from the feature for each incident angle in the set of angles, and a processor for determining a discontinuity in the intensities as a function of the incident angle.

Another embodiment of the invention relates to an apparatus for measuring an undercut of a feature on a specimen. The apparatus includes means for illuminating the feature with a primary electron beam at an incident angle, means for changing the incident angle of the primary electron beam over a set of angles, means for measuring an intensity of scattered electrons from the feature for each incident angle in the set of angles, and means for determining a discontinuity in the intensities as a function of the incident angle.

DETAILED DESCRIPTION

The present invention relates to a technique for measuring undercut angles in an advantageously non-destructive manner. The technique may be performed using a scanning electron microscope and may be applied to measure undercut angles of features on a semiconductor wafer or other types of specimens. In accordance with one embodiment, even if the images have substantial resolution degradation (due to large rock angles), the technique may still be applied to measure undercut angles.

Figure 2:
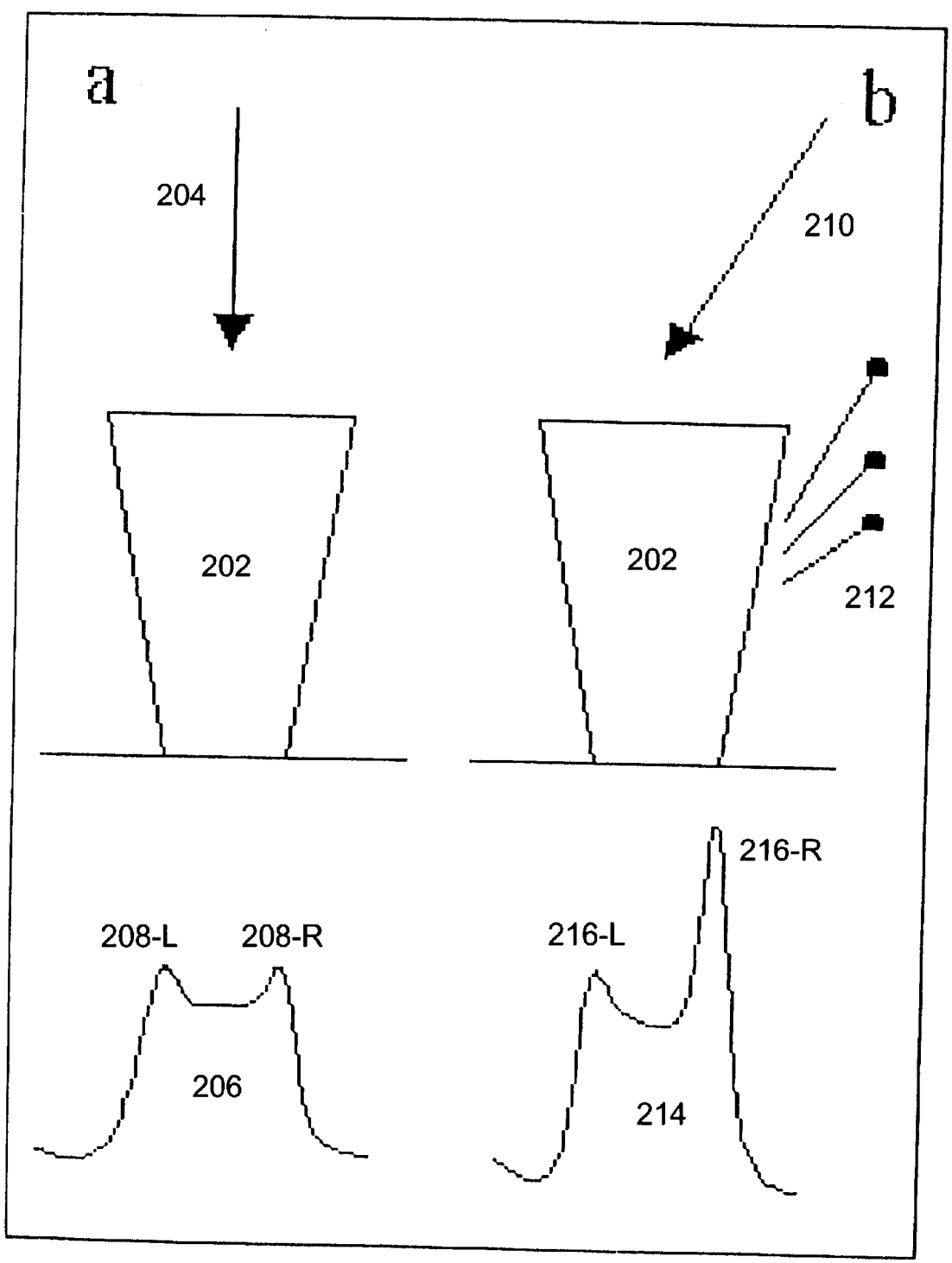
FIG. 2 is a diagram providing an overview of the technique for measuring undercut angles in accordance with an embodiment of the invention.

FIG. 2 is a diagram providing an overview of the technique for measuring undercut angles for an undercut feature 202 in accordance with an embodiment of the invention. An electron beam 204 with an incident angle of less than the undercut angle (for example, zero degrees) is illustrated on the left side (situation labeled "a"), and an electron beam 210 with an incident angle that is greater than the undercut angle is illustrated on the right side (situation labeled "b"). Corresponding electron intensity profiles 206 (for situation "a") and 214 (for situation "b") are depicted below.

For situation "a", the electron intensity profile 206 for the feature 202 is seen to be relatively symmetrical. There is a peak 208-L on the left side of the profile 206 and a nearly equal sized peak 208-R on the right side. These peaks in electron intensities are believed by the applicants to be due to emission and collection of scattered electrons from the sidewalls of the feature 202.

For situation "b", the electron intensity profile 214 for the feature 202 is seen to be substantially asymmetrical. The right-side peak 216-R is now substantially higher than the left-side peak 216-L. This asymmetry is believed by the applicants to be due to the electron beam 210 being incident from the right side at an angle exceeding the undercut angle of the right sidewall. As a result, it is believed that the incident beam 210 directly illuminates the right sidewall and so causes the emission of a greater number of scattered electrons 212.

Figure 1A:
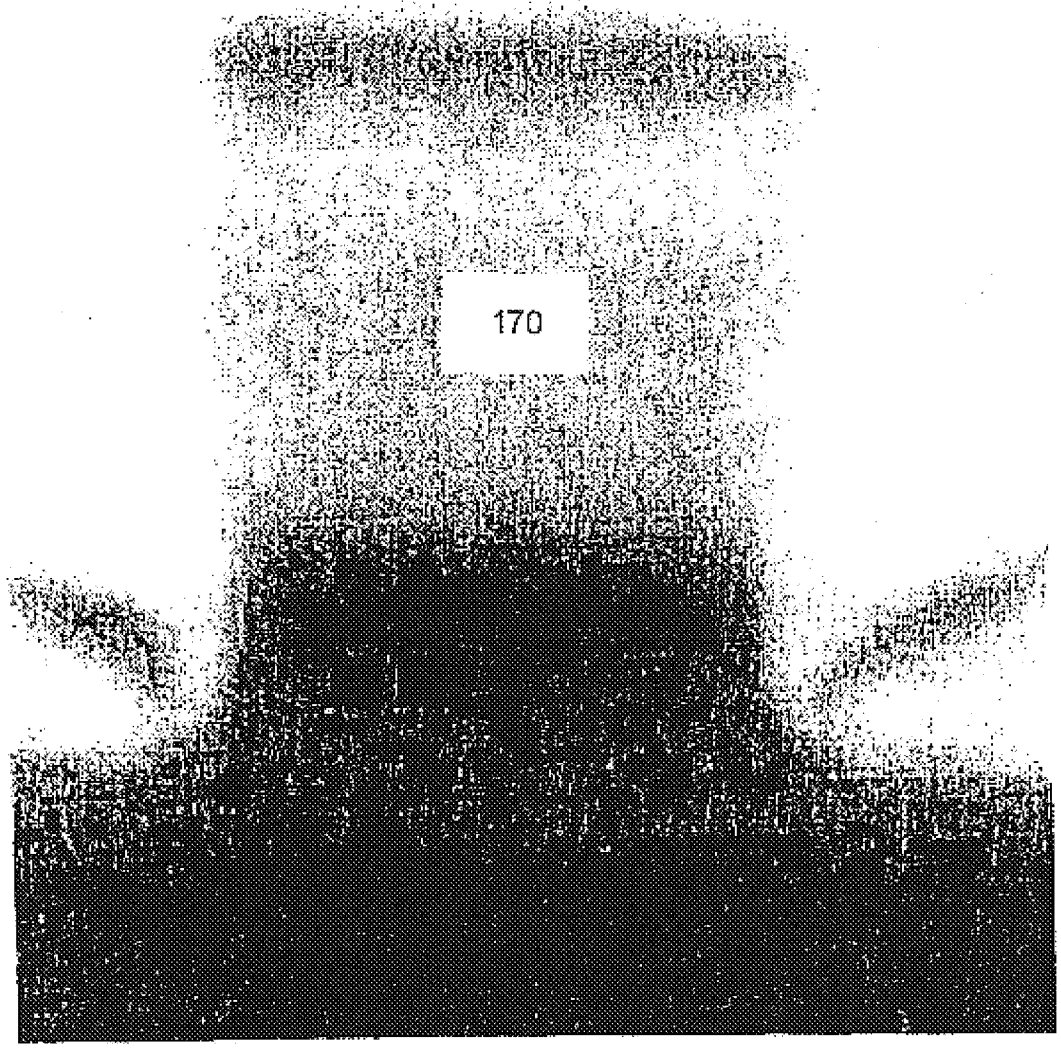
FIG. 1A is a conventional image of a cross section of a feature that is slightly undercut on both left and right sides.
Figure 1B:
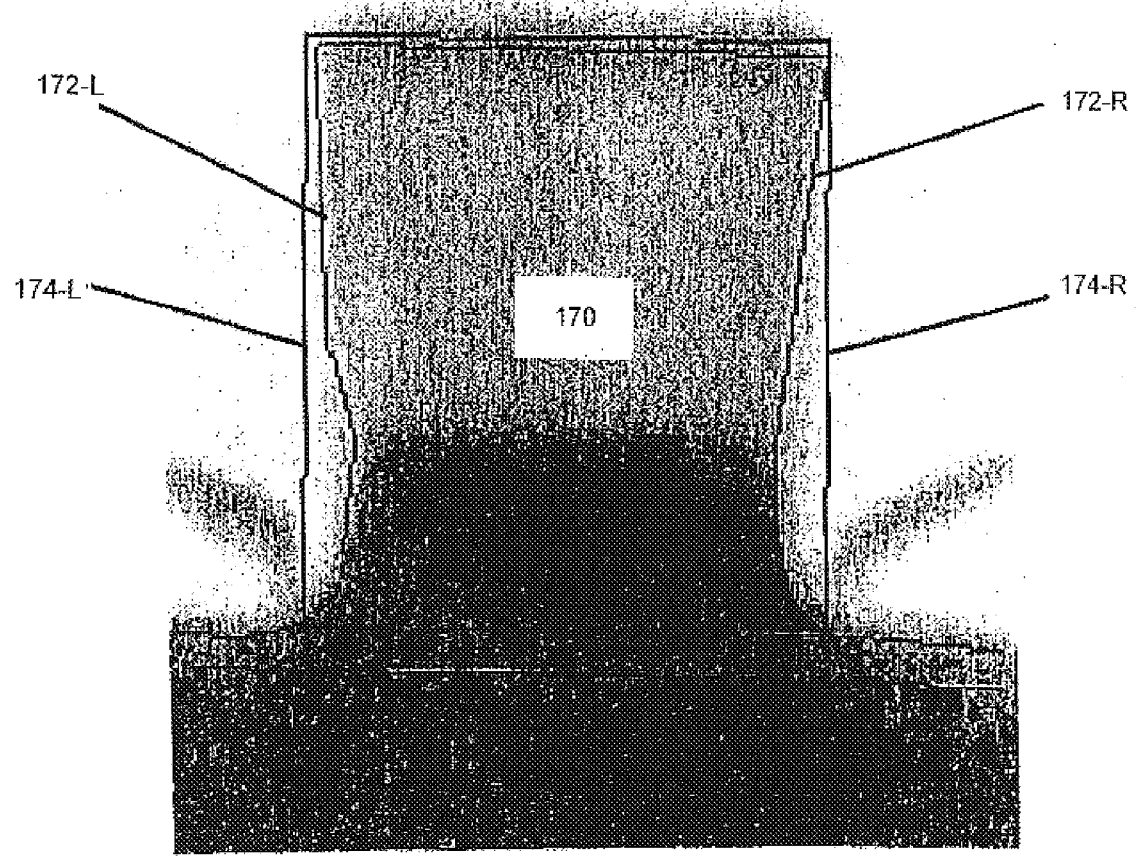
FIG. 1B shows a conventional analysis of the cross-sectional FIB image of the feature to determine the undercut angles.
Figure 3A:
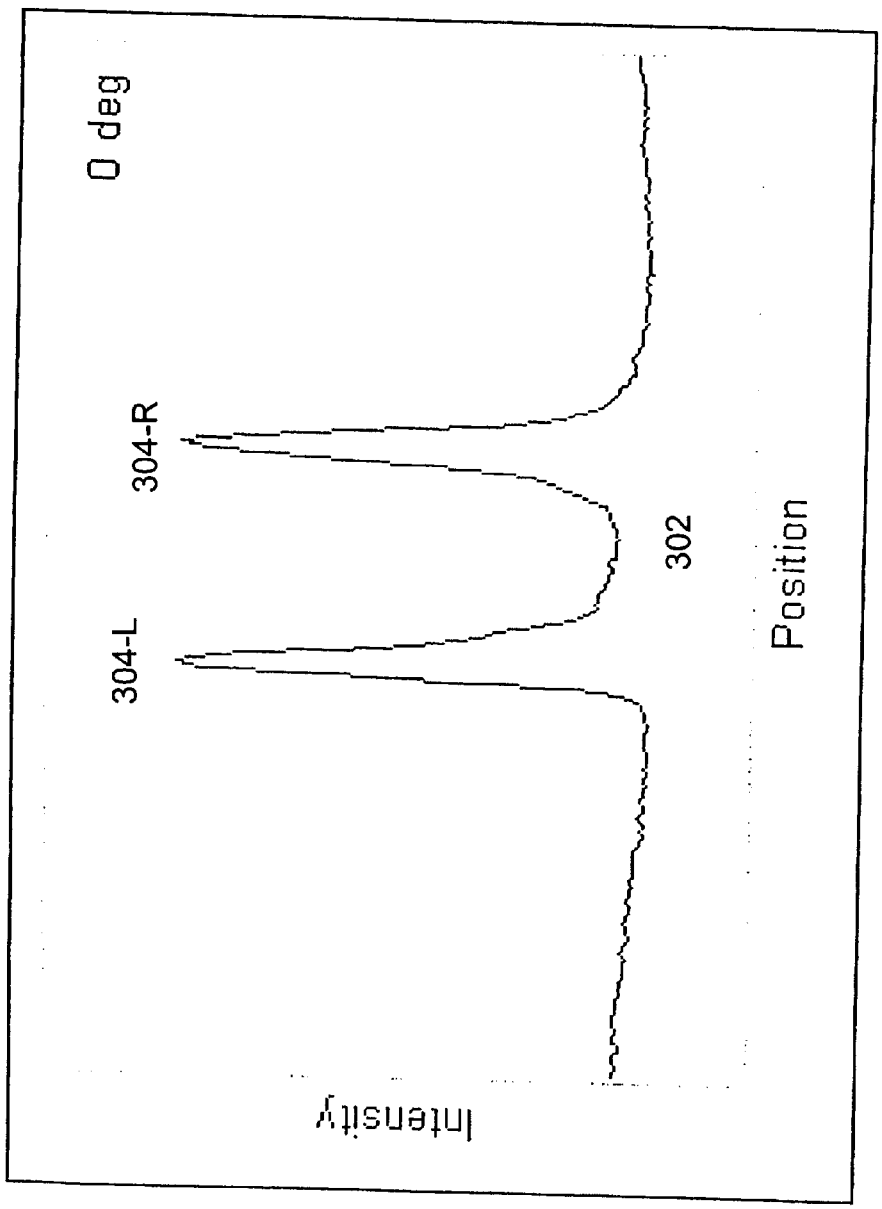
FIGS. 3A and 3B shown experimental electron scans of the undercut feature depicted in FIGS. 1A and 1B.
Figure 3B:
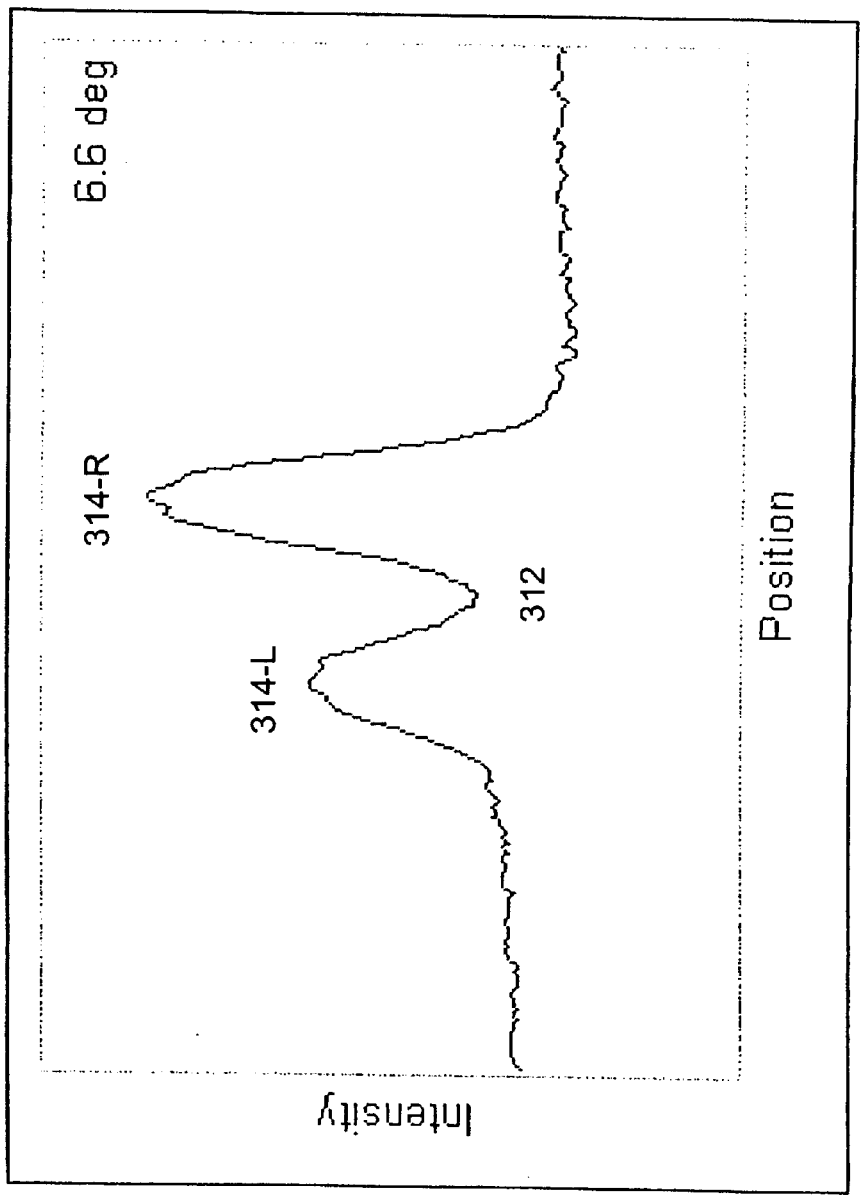

FIGS. 3A and 3B show experimental electron scans of the undercut feature 170 depicted in FIGS. 1A and 1B. The beam tilt was at zero degrees for FIG. 3A and was at 6.6 degrees for FIG. 3B. Both FIGS. 3A and 3B show electron intensity versus position in the region of the undercut feature 170. The electron scans of FIGS. 3A and 3B do not require destruction of the specimen and were performed prior to the destructive FIB cross sectioning of FIGS. 1A and 1B. By using the present invention, undercut angles may be determined without the use of destructive FIB sectioning.

As can be seen from FIG. 3A, the electron intensity profile 302 for the feature 170 is seen to be relatively symmetrical. There is a peak 304-L on the left side of the profile 302 and a nearly equal sized peak 304-R on the right side. The symmetry shown is expected given the zero degree incidence angle of the primary electron beam.

On the other hand, in FIG. 3B, the electron intensity profile 312 for the feature 170 is seen to be asymmetrical. The right-side peak 314-R is now substantially higher than the left-side peak 314-L. This asymmetry is believed by the applicants to be due to the electron beam being incident from the right side at an angle (6.6 degrees) that exceeds the undercut angle of the right sidewall (approximately 4 degrees). As a result, it is believed that the incident beam directly illuminates the right sidewall and so causes the emission of a greater number of scattered electrons. In accordance with an embodiment of the invention, it may be determined from FIGS. 3A and 3B that the undercut angle is somewhere between zero degrees and 6.6 degrees.

Note that the peaks are wider in FIG. 3B than the peaks in FIG. 3A. This broadening of the peaks corresponds to the blurring of the detected image that occurs when the incident beam is tilted in the SEM. It is believed that this blurring that makes the asymmetry between right and left intensities difficult to detect visually from the scanned image. Hence, a preferred embodiment of the invention quantitatively analyzes the scanned data.

Figure 4A:
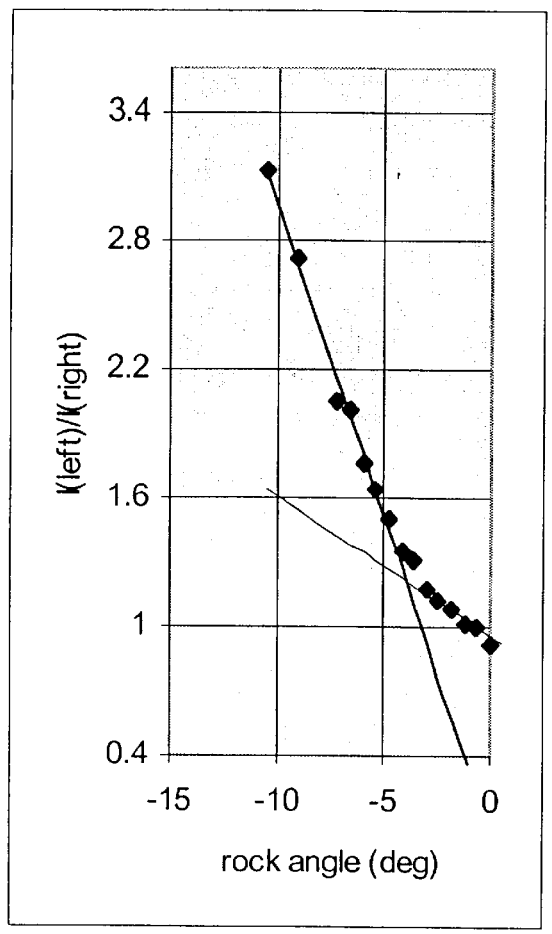
FIG. 4A is a graph showing the analysis of data from a series of electron scans at different incidence angles to measure the left undercut in accordance with an embodiment of the invention.

FIG. 4A is a graph showing the analysis of data from a series of electron scans at different incidence angles to measure the left undercut in accordance with an embodiment of the invention. The y-axis shows the ratio between the left peak intensity I(left) and the right peak intensity I(right). The x-axis shows the incidence angle of the primary beam (the rock angle) in degrees. In a preferred embodiment, the peak intensities are measured by the peak heights. However, in other embodiments, it may be possible also to measure the peak intensities using integrated peak areas. In the graph of FIG. 4A, we see that there is a discontinuity in the slope of the data at an incident angle of about −4 degrees. This indicates that the left undercut is approximately 4 degrees. This is in relatively close agreement with the FIB cross section measured left undercut of about 5 degrees.

Figure 4B:
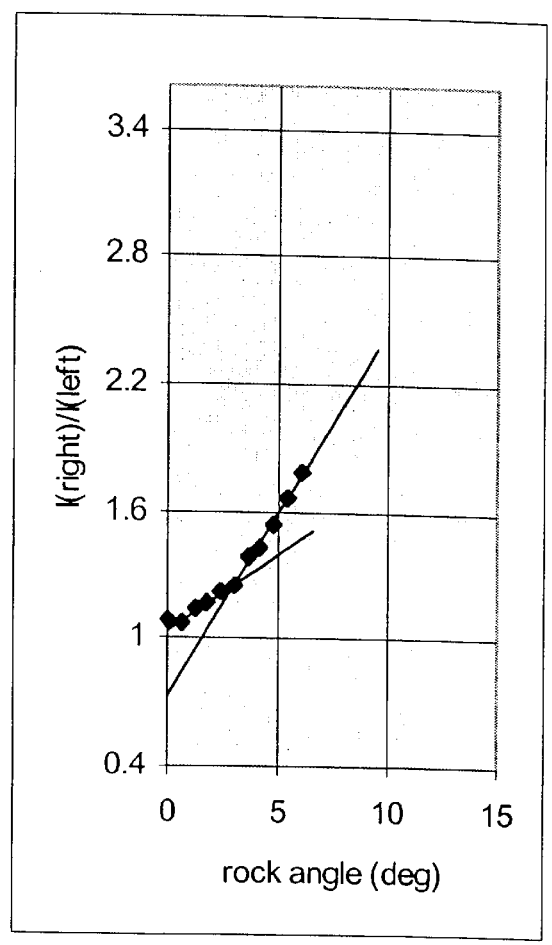
FIG. 4B is a graph showing the analysis of data from a series of electron scans at different incidence angles to measure the right undercut in accordance with an embodiment of the invention.

FIG. 4B is a graph showing the analysis of data from a series of electron scans at different incidence angles to measure the right undercut in accordance with an embodiment of the invention. The y-axis shows the ratio between the right peak intensity I(right) and the left peak intensity I(left). The x-axis shows the incidence angle of the primary beam (the rock angle) in degrees. In the graph of FIG. 4B, we see that there is a discontinuity in the slope of the data at an incident angle of about +3 degrees. This indicates that the right undercut is approximately 3 degrees. This is in relatively close agreement with the FIB cross section measured left undercut of about 2 degrees.

Figure 5A:
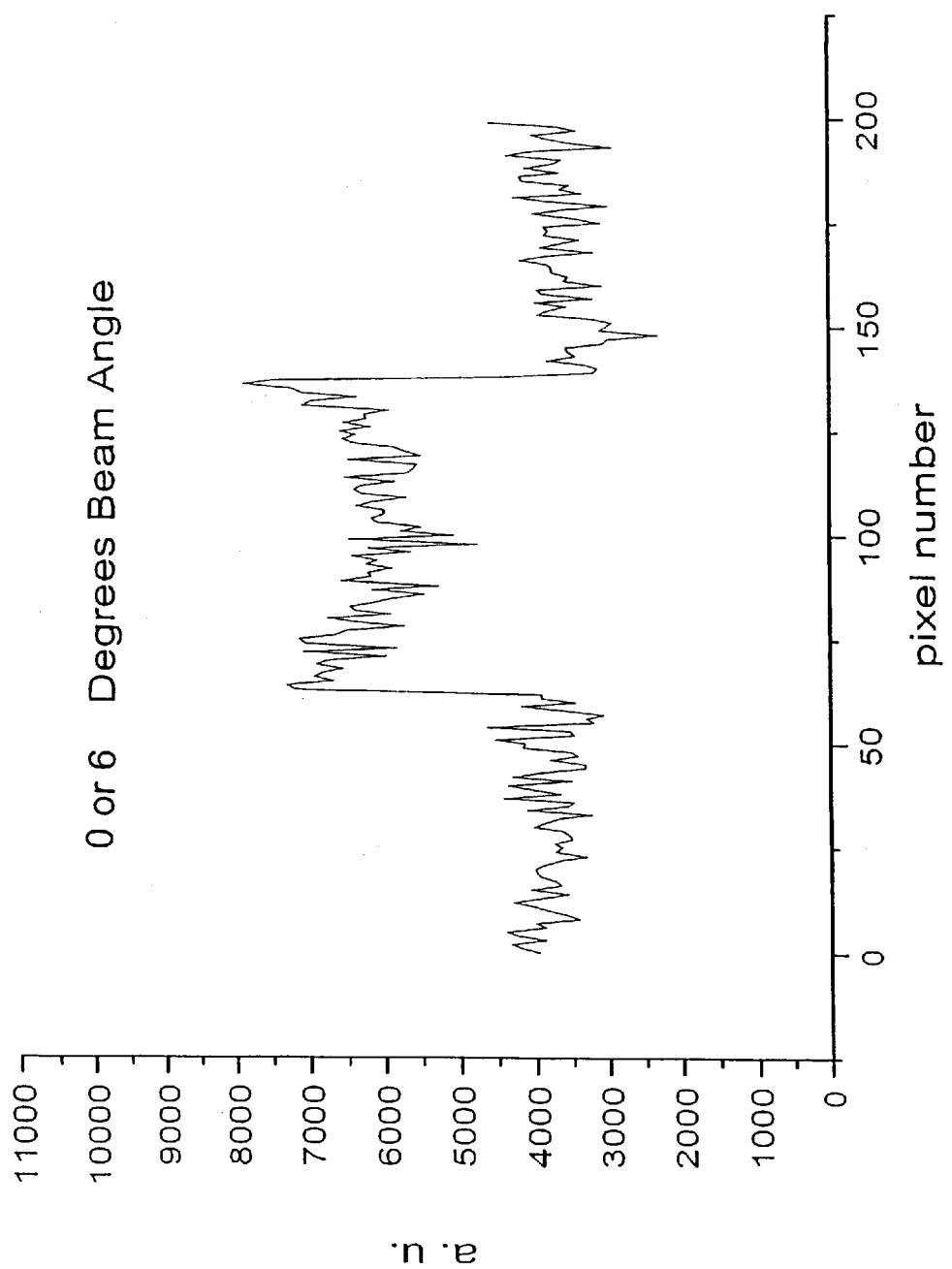
FIGS. 5A through 5D depict simulated electron scans based on a hypothetical feature with ten-degree undercuts on each side.
Figure 5B:
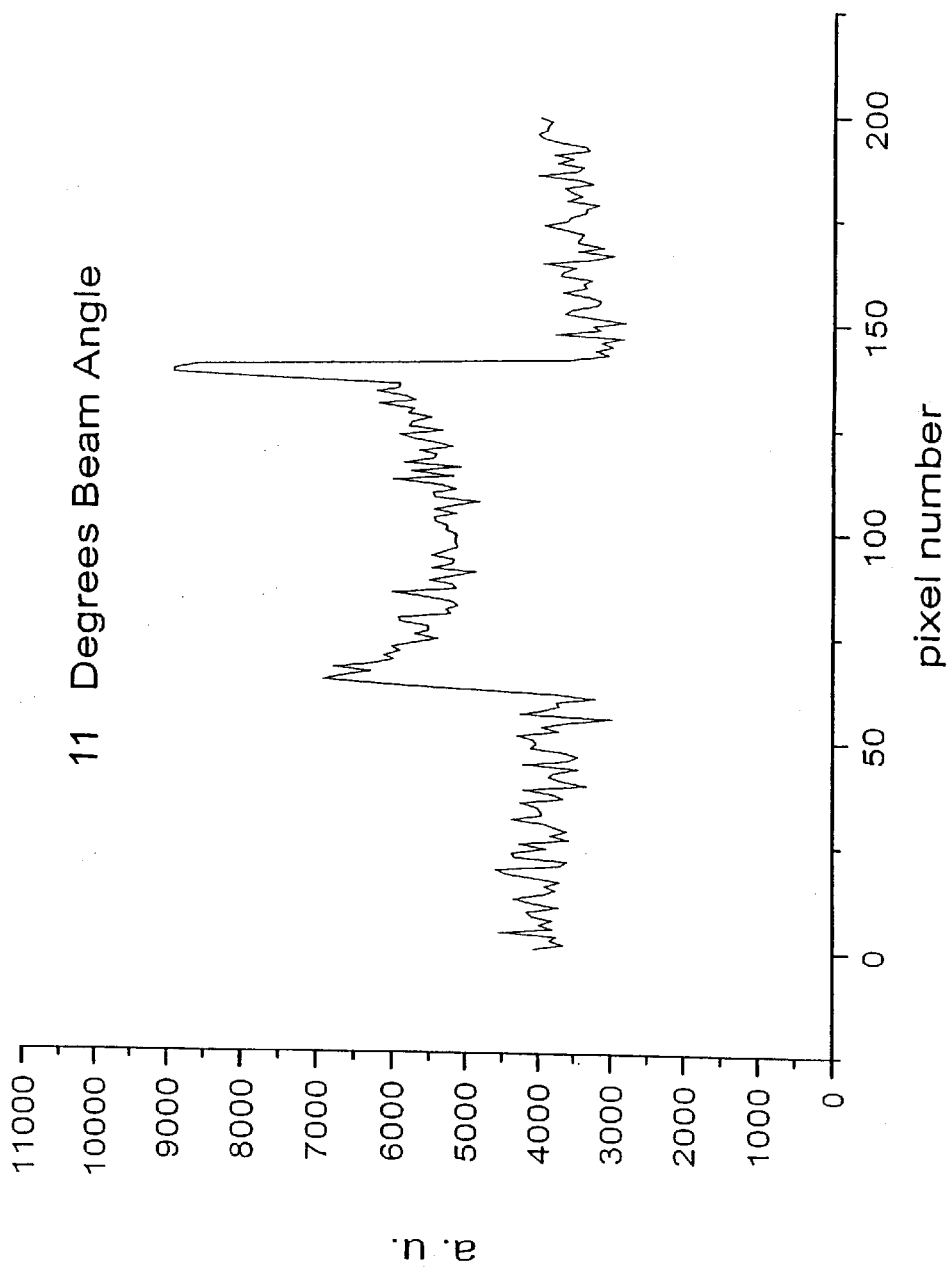
Figure 5C:
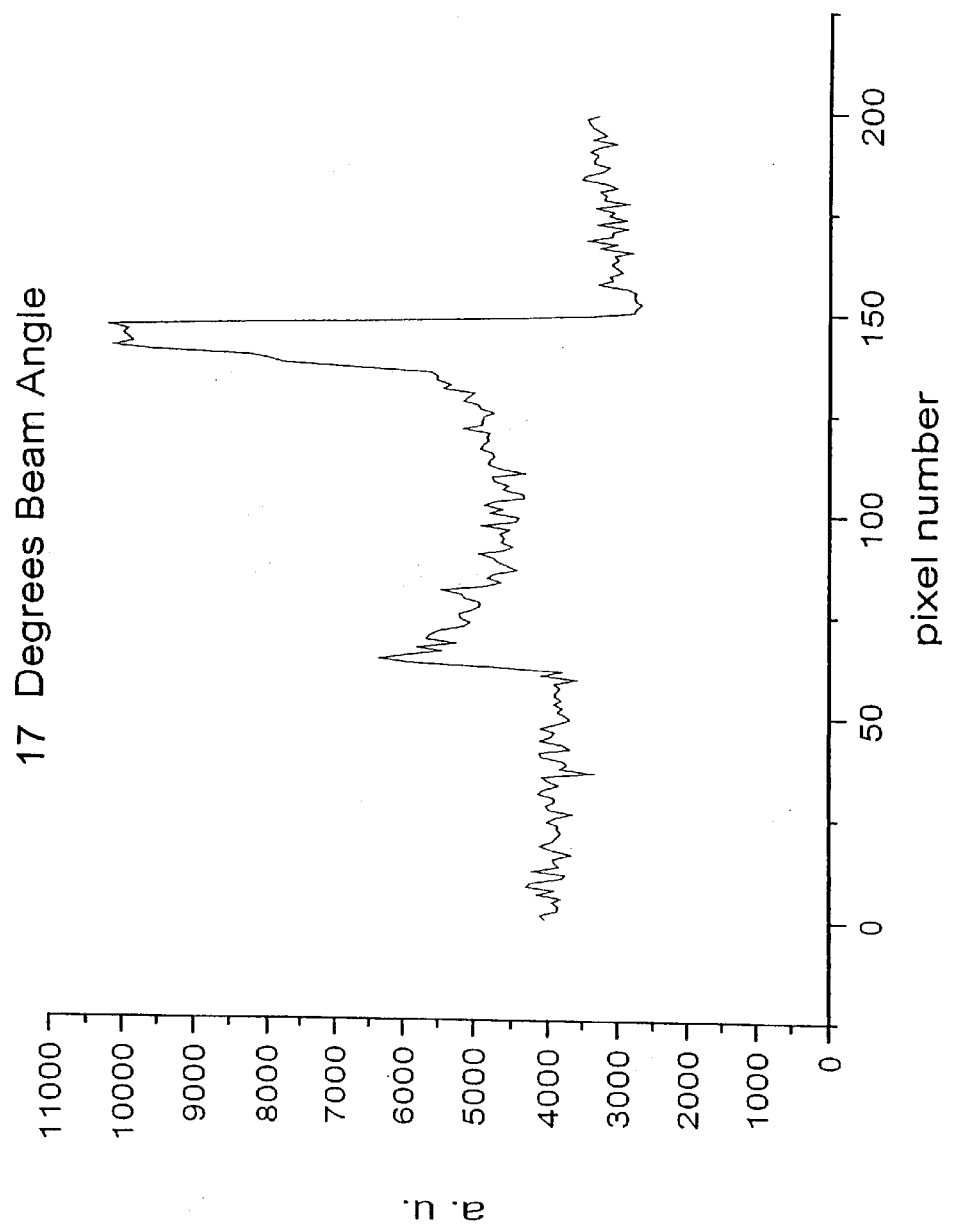
Figure 5D:
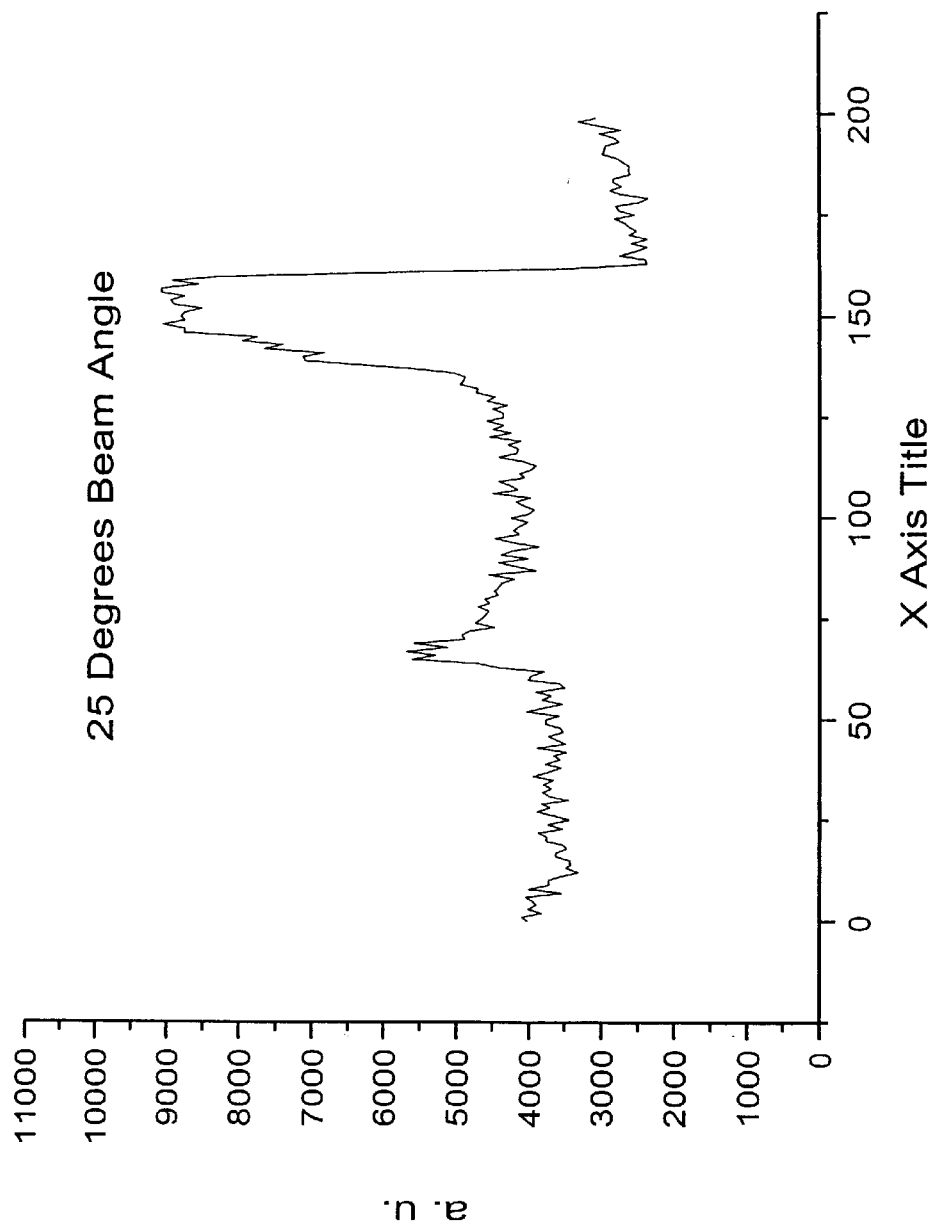

FIG. 5A through 5D depict simulated electron scans based on a hypothetical feature with ten-degree undercuts on each side. Each of these figures depicts electron intensity (in arbitrary units) on the y-axis as a function of position on the x-axis. FIG. 5A corresponds to low incident angles of six degrees or less and shows a relatively symmetrical profile. FIG. 5B corresponds to an incident angle of eleven degrees and shows asymmetry in that the right peak is higher than the left peak. FIG. 5C corresponds to an incident angle of seventeen degrees and shows the asymmetry increasing as the right peak becomes even higher. Finally, FIG. 5D corresponds to an incident angle of twenty-five degrees and shows that a reduction in asymmetry as the right peak is lower than in FIG. 5C. Thus, FIG. 5D shows that the asymmetry does not continue to increase at very high angles.

Figure 6:
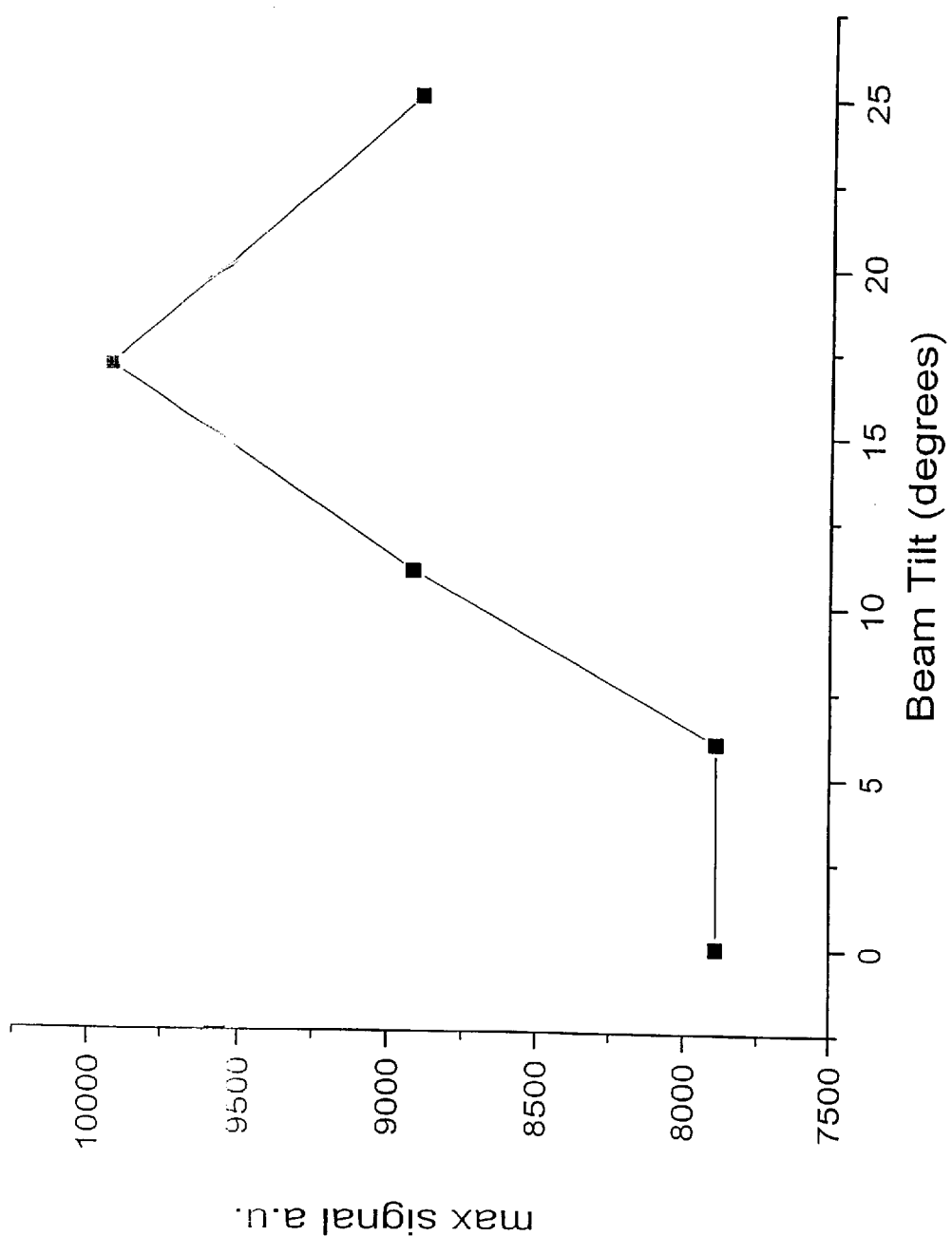
FIG. 6 is a graph showing the analysis of the simulated data from FIGS. 5A through 5D in accordance with an embodiment of the invention.

FIG. 6 is a graph showing the analysis of the simulated data from FIGS. 5A through 5D in accordance with an embodiment of the invention. Data points in FIG. 6 are at zero degrees (from FIG. 5A), six degrees (from FIG. 5A), eleven degrees (from FIG. 5B), seventeen degrees (from FIG. 5C), and twenty-five degrees (from FIG. 5D). As indicated from FIG. 6, the undercut angle is between six degrees and eleven degrees. This is a good result because the simulations are based on an undercut angle of ten degrees. Of course, further simulations at closer angles may be performed to more precisely determine the undercut angle.

Figure 7:
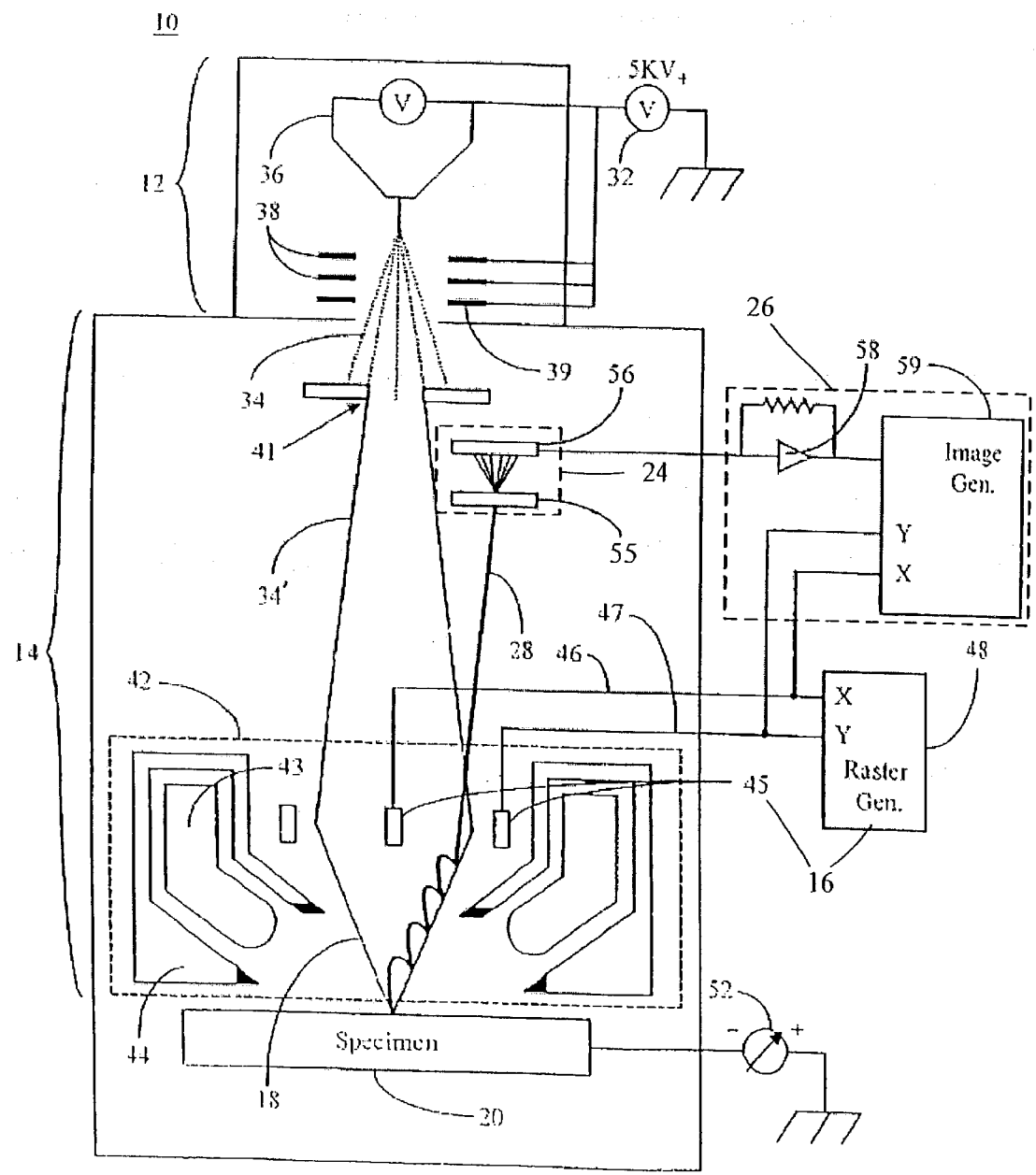
FIG. 7 depicts one type of SEM system with which the invention may be utilized.
Figure 8:
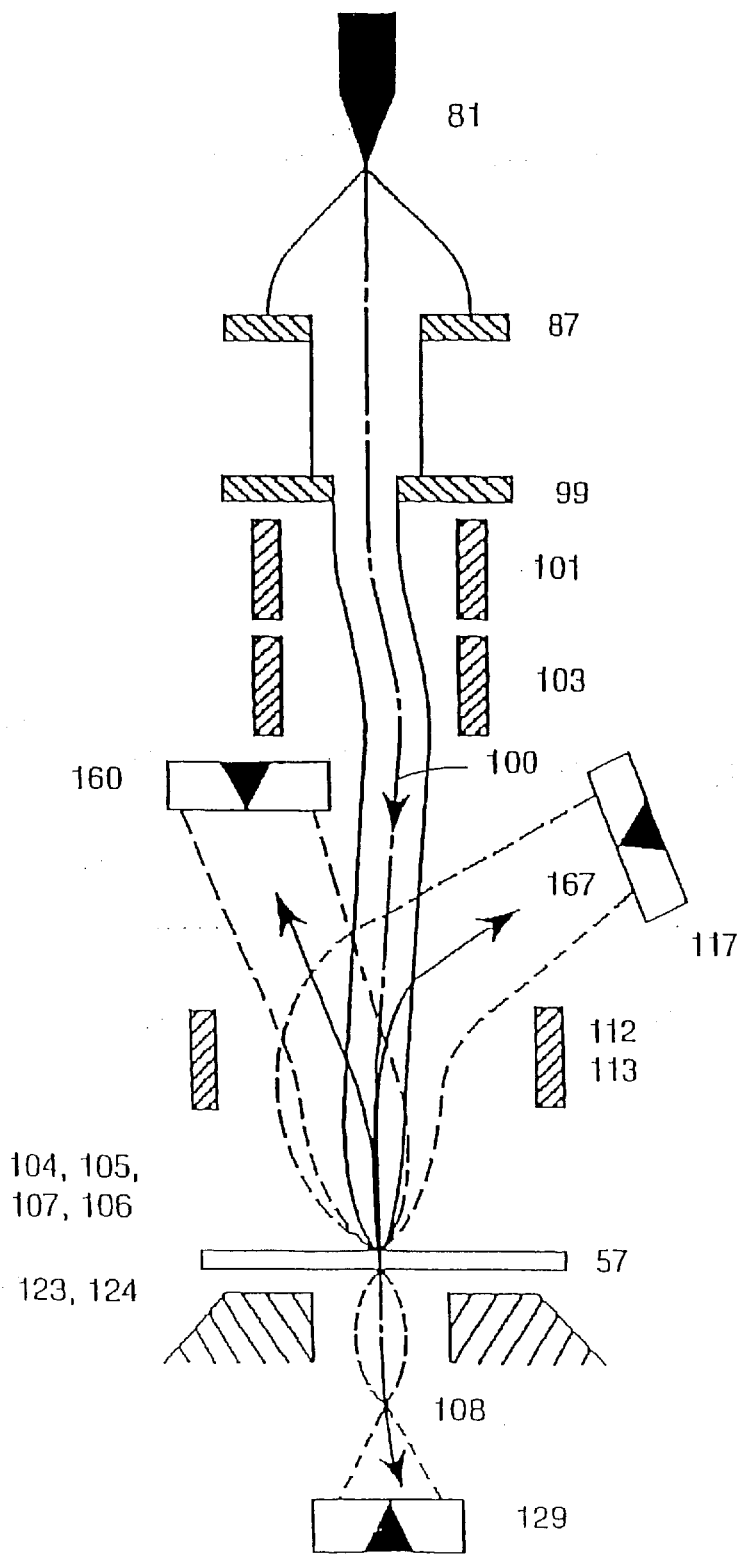
FIG. 8 depicts another type of SEM system with which the invention may be utilized.

Scanning electron microscope (SEM) systems are shown in FIGS. 7 and 8 as examples of SEM systems with which the invention may be utilized. The present invention may be utilized in other types of SEM systems as well.

The SEM system 10 depicted in FIG. 7 is particularly suitable for measurement of critical dimensions and is described in detail in U.S. Pat. No. 5,869,833, entitled "Electron Beam Dose Control for Scanning Electron Microscopy and Critical Dimension Measurement Instruments," issued to Richardson et al. and assigned to KLA-Tencor Corporation of San Jose, Calif. The disclosure of U.S. Pat. No. 5,869,833 (the Richardson patent) is hereby incorporated by reference.

The SEM 10 of FIG. 7 includes an electron beam source 12, a focusing column and lens assembly 14, and a scan controller 16. The scan controller 16 scans an electron beam across selected regions of the specimen 20. Also included is a detector subsystem 24 to detect secondary and backscattered electrons from the specimen 20.

The electron beam source 12 at the top of the SEM system 10 produces an electron beam 34. One implementation that could be used includes an electron source 36 that consists of a thermal field emitter with electrons accelerated by a surface field generated by power supply 32. Alternative electron source embodiments may instead be employed. The electrons emitted by the electron source 36 are then, within the beam source 12, directed through the electrodes 38 and the source lens 39 (each also controlled by the power supply 32) to form the electron beam 34 that enters the focusing column and lens assembly 14 to be directed to the specimen 20.

In the focusing column and lens assembly 14, the electron beam 34 passes through an aperture 41, reducing the beam current. For example, the beam current may be reduced from approximately 300 pA (pico Amperes) to a range of 5 to 100 pA forming the electron beam that is labeled 34'. The electron beam 34' then passes through an objective lens 42 that includes magnetic coils 43 and pole pieces 44 to generate a strong magnetic field. That magnetic field is used to focus beam 34' into an electron beam 18 with a spot size that may be, for example, about 5 nm (nanometers) when directed at the specimen 20. A bias may be applied by a power supply 52 to the specimen 20 to create a decelerating field to slow down the electrons in the beam 18 as the electrons approach the specimen 20.

In operation, the electron beam 18 may be raster scanned over the specimen 20 and the secondary and backscattered electron signal 28 may be detected by the detector subsystem 24. The secondary and backscattered electrons 28 are released as a result of the interaction of the electron beam 18 with specimen 20 and are directed back toward the objective lens 42. As electrons 28 are released, they may spiral through the objective lens 42 (as a result of the magnetic field), and then travel toward the detector subsystem 24 as they leave the field within the lens 42. Typically, the specimen 20 may be comprised of a variety of materials that may be conductive, insulating, or semi-conducting. A sub-area within the specimen 20 may be of particular interest for scanning to determine features of that sub-area. An image processor and display subsystem 26 may develop the image of the sub-area. For example, the specimen 20 may be a semiconductor wafer and a sub-area of the wafer may be a portion of a circuit die on the wafer.

The detector subsystem 24 may be selected to have a bandwidth that is at least adequate to detect the secondary and backscattered electrons that form the electron signal 28. For example, the detector subsystem 24 may include a micro-channel plate, micro-sphere plate, semiconductor diode, or a scintillator and photo-multiplier assembly. The detector subsystem 24 illustrated in FIG. 7 includes a detector 55 and collector plat 56. The secondary and backscattered electron signal 28 is received by the detector 55 and then collected by the collector plate 56. The collector plate 56 generates a signal that is received by the image processor and display subsystem 26. The image processor and display subsystem 26 may amplify the signal by an amplifier 58 before the signal is input into an image generator 59.

The location of the electron beam 18 on the specimen 20 is controlled by the scan controller 16. The scan controller 16 illustrated in FIG. 7 includes scan plates 45 that are located within the magnetic field created by coils 43 and pole pieces 44. The scan plates 45 are powered by a raster generator 48 (via signals on lines 46 and 47) to direct the electron beam 18 in both the x and y directions across the specimen 20.

The SEM system depicted in FIG. 8 is described in U.S. Pat. No. 5,578,821, entitled "Electron Beam Inspection System and Method," issued to Meisberger et al. and assigned to KLA-Tencor Corporation of San Jose, Calif. The disclosure of U.S. Pat. No. 5,578,821 (the Meisberger patent) is hereby incorporated by reference.

FIG. 8 is a simplified schematic representation of the paths of the primary, secondary, backscattered and transmitted electrons through the electron optical column and collection system for electron beam inspection. In brief, FIG. 8 shows a schematic diagram of the various electron beam paths within the column and below substrate 57. Electrons are emitted radially from field emission cathode 81 and appear to originate from a very small bright point source. Under the combined action of the accelerating field and condenser lens magnetic field, the beam is collimated into a parallel beam. Gun anode aperture 87 masks off electrons emitted at unusable angles, while the remaining beam continues on to beam limiting aperture 99. An upper deflector (not depicted) is used for stigmation and alignment, ensuring that the final beam is round and that it passes through the center of the objective lens 104 comprising elements 105, 106 and 107. A condenser lens (not depicted) is mechanically centered to the axis defined by cathode 81 and beam limiting aperture 99. The deflection follows the path shown, so that the scanned, focused probe (beam at point of impact with the substrate) emerges from the objective lens 104.

In High Voltage mode operation, Wien filter deflectors 112 and 113 deflect the secondary electron beam 167 into detector 117. When partially transparent masks are imaged, the transmitted beam 108 passes through electrode system 123 and 124 that spreads the beam 108 before it hits the detector 129. In Low Voltage mode operation, the secondary electron beam is directed by stronger Wien filter deflections toward the low voltage secondary electron detector 160 that may be the same detector used for backscatter imaging at high voltage. Further detail on the system and its operation is described in the Meisberger patent.

In accordance with one embodiment of the invention, the incidence angle of the primary electron beam may be varied by appropriate adjustment of the currents in the objective lenses that focus the beam onto the specimen. In accordance with another embodiment of the invention, the incidence angle of the primary electron beam may be varied by tilting the stage holding the specimen. Advantageously, this embodiment may avoid the blurring of the scanned image that occurs when the incident beam is tilted.

In accordance with an alternate embodiment, electron detection at a range of angles may be used to measure the undercut angle. Such an embodiment may include multiple electron detectors at different scattering angles and application of a non-uniform extracting field to differentiate between scattered electrons at the different scattering angles. The multiple detectors would be oriented such that the sidewall of interest is within direct line-of-sight of the detectors at higher detecting angles so that a discontinuity occurs between a first detector without direct line-of-sight and a second detector with direct line-of-sight. In that case, the measured undercut angle may correspond to the detecting angle at which the discontinuity is determined to occur.

In the above description, numerous specific details are given to provide a thorough understanding of embodiments of the invention. However, the above description of illustrated embodiments of the invention is not intended to be exhaustive or to limit the invention to the precise forms disclosed. One skilled in the relevant art will recognize that the invention can be practiced without one or more of the specific details, or with other methods, components, etc. In other instances, well-known structures or operations are not shown or described in detail to avoid obscuring aspects of the invention. While specific embodiments of, and examples for, the invention are described herein for illustrative purposes, various equivalent modifications are possible within the scope of the invention, as those skilled in the relevant art will recognize.

These modifications can be made to the invention in light of the above detailed description. The terms used in the following claims should not be construed to limit the invention to the specific embodiments disclosed in the specification and the claims. Rather, the scope of the invention is to be determined by the following claims, which are to be construed in accordance with established doctrines of claim interpretation.

What is claimed is:

1. A method for measuring an undercut of a feature on a specimen using a scanning electron microscope (SEM), the method comprising:
    illuminating the feature with a primary electron beam at an incident angle;
    changing the incident angle of the primary electron beam over a set of angles;
    measuring a peak intensity of scattered electrons from a peak at an edge of the feature for each incident angle in the set of angles; and
    determining a discontinuity in the peak intensifies as a function of the incident angle.

2. The method of claim 1, wherein the set of angles is oriented such that at higher incident angles the primary electron beam impinges directly upon a sidewall of the feature.

3. The method of claim 2, wherein the discontinuity occurs when the primary electron beam begins to impinge directly upon the sidewall.

4. The method of claim 3, wherein the measured undercut angle corresponds to the incident angle at which the discontinuity is determined to occur.

5. The method of claim 1, wherein the determining is performed using a computer-implemented process.

6. The method of claim 1, wherein the peak intensities are measured based on peak heights.

7. The method of claim 1, wherein the peak intensities are measured based on integrated peak areas.

8. The method of claim 1, wherein the incident angle is changed by tilting a primary electron beam.

9. The method of claim 1, wherein the incident angle is changed by tilting a specimen stage.

10. The method of claim 1, wherein the SEM comprises an SEM configured for measuring critical dimensions (CD-SEM).

11. A method for measuring an undercut of a feature on a specimen using a scanning electron microscope (SEM), the method comprising:
    illuminating the feature with primary electrons at an incident angle;
    measuring a peak intensity of scattered electrons from a peak at an edge of the feature by a plurality of detectors at a set of scattering angles; and
    determining a discontinuity in the peak intensities as a function of the scattering angle.

12. The method of claim 11, further comprising:
    applying a non-uniform extracting field to differentiate between scattered electrons at different scattering angles.

13. The method of claim 12, wherein the plurality of detectors are oriented such that a sidewall of the feature is within direct line-of-sight of detectors at higher detecting angles.

14. The method of claim 13, wherein the discontinuity occurs between a first detector without direct line-of-sight and a second detector with direct line-of-sight.

15. The method of claim 14, wherein the measured undercut angle corresponds to the detecting angle at which the discontinuity is determined to occur.

16. The method of claim 11, wherein the determining is performed using a computer-implemented process.

17. A scanning electron microscope (SEM) for measuring an undercut of a feature on a specimen, the SEM comprising:
    an electron illumination system for illuminating the feature with a primary electron beam at an incident angle;
    a mechanism for changing the incident angle of the primary electron beam over a set of angles;
    a detector for measuring a peak intensity of scattered electrons from a peak at an edge of the feature for each incident angle in the set of angles; and
    a processor for determining a discontinuity in the peak intensities as a function of the incident angle.

18. The SEM of claim 17, wherein the mechanism for changing the incident angle comprises an adjustable electromagnet lens system for tilting the primary electron beam with respect the specimen.

19. The SEM of claim 18, wherein the mechanism for engaging the incident angle comprises tiltable stage for tilting the specimen with respect to the primary electron beam.

20. An apparatus for measuring an undercut of a feature on a specimen, the apparatus comprising:
    means for illuminating the feature with a primary electron beam at an incident angle;
    means for changing the incident angle of the primary electron beam over a set of angles;
    means for measuring a peak intensity of scattered electrons from a peak at an edge of the feature for each incident angle in the set of angles; and
    means for determining a discontinuity in the peak intensities as a function of the incident angle.

* * * * *